(12) United States Patent
Nagano et al.

(10) Patent No.: US 6,656,927 B1
(45) Date of Patent: Dec. 2, 2003

(54) IP$_3$ RECEPTOR LIGANDS

(75) Inventors: Tetsuo Nagano, 1-28-15, Amanuma, Suginami-ku, Tokyo 167-0032 (JP); Kazuya Kikuchi, Kanagawa (JP); Takanari Inoue, Kanagawa (JP); Masamitsu Iino, Tokyo (JP); Kenzo Hirose, Tokyo (JP)

(73) Assignees: Tetsuo Nagano, Tokyo (JP); Daiichi Pharmaceutical., Ltd., Tokyo (JP)

( * ) Notice: Subject to any disclaimer, the term of this patent is extended or adjusted under 35 U.S.C. 154(b) by 0 days.

(21) Appl. No.: 09/926,664

(22) PCT Filed: May 25, 2000

(86) PCT No.: PCT/JP00/03344

§ 371 (c)(1),
(2), (4) Date: Nov. 30, 2001

(87) PCT Pub. No.: WO00/75150

PCT Pub. Date: Dec. 14, 2000

(30) Foreign Application Priority Data

Jun. 2, 1999 (JP) ............................................ 11-154528

(51) Int. Cl.$^7$ ........................ A61K 38/00; A61K 31/35; C07F 9/06; C09B 11/06; C09B 11/10
(52) U.S. Cl. ........................ 514/100; 514/454; 549/220; 552/107; 552/113
(58) Field of Search ................................ 514/100, 454; 549/220; 552/107, 113

(56) References Cited

PUBLICATIONS

Habel et al, Feb. 1998, "Human osteoblast–like cells respond not only to the extracellular calcium concentration but also to its changing rate", Eur. Biophys. Jol., vol. 27 pp 411–416 (1998).*
Berridge, M., Nature 361, pp. 315–325 (1993).
Clapham, D., Cell 80, pp. 259–268 (1995).
Li, W–h., et al., Nature 392, pp. 936–941 (1998).
McCarran, M., et al., Neuron 3, pp. 461–471 (1989).
Mourey, R., et al., Biochemistry 32, pp. 1719–1726 (1993).
Schäfer, R., et al., Biochem. J. 272, pp. 817–825 (1990).
Prestwich, G., et al., J. Am. Chem. Soc. 113, pp. 1822–1825 (1991).

(List continued on next page.)

Primary Examiner—Al Rotman
Assistant Examiner—Raymond Covington
(74) Attorney, Agent, or Firm—Greenblum & Bernstein, P.L.C.

(57) ABSTRACT

A compound represented by the general formula (I) or a salt thereof, wherein R represents a group represented by the following formula (A), (B) or (C) wherein $R^1$ and $R^2$ independently represent a $C_{1-6}$ alkyl group, $R^3$ represents an amino group, a mono($C_{1-6}$ alkyl)amino group, a di($C_{1-6}$ alkyl)amino group or a $C_{1-6}$ alkoxy group and X-represents an anion, and n represents an integer of 2 to 5. The compound or a salt is useful as a ligand of inositol-1,4,5-trisphosphate (IP$_3$) receptor.

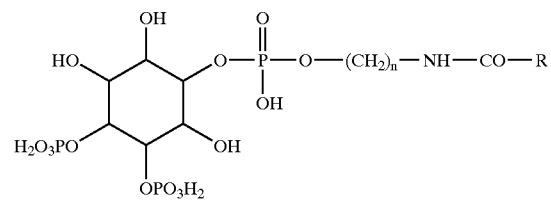

(I)

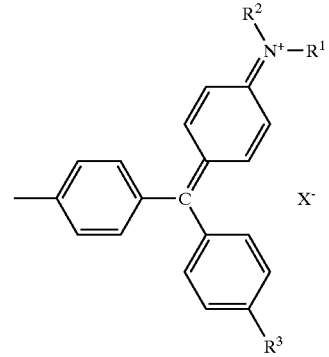

(A)

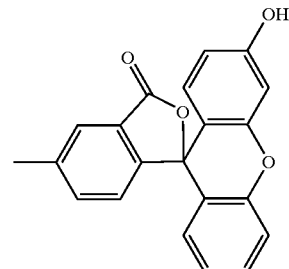

(B)

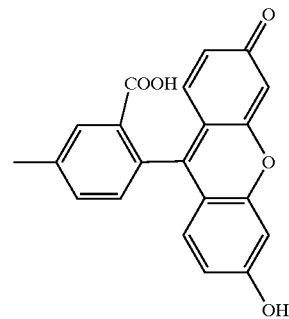

(C)

24 Claims, 2 Drawing Sheets

OTHER PUBLICATIONS

Takahashi, M., et al., J. Biol. Chem. 269, pp. 369–372 (1994).

Strupish, J. et al., Biochem. J. 253, pp. 901–905 (1988).

Ozaki, S. et al., J. Chem. Soc. Perkins Trans. I, pp. 729–737 (1992).

Gigg, J., et al., J. Chem. Soc. Perkins Trans. I, pp. 423–429 (1987).

Bannawarth, W., and Trzeciak, A., Helvetica Chimica Acta 70, pp. 175–187 (1987).

Radenburg, T., et al., Biochem. J. 264, pp. 323–333 (1989).

Mignery, G., and Südhof, T. EMBO 9, pp. 3893–3898 (1990).

Yamada, N., et al., Biochem J. 302, pp. 781–790 (1994).

* cited by examiner

IP₃ RECEPTOR LIGANDS

TECHNICAL FIELD

The present invention relates to a ligand of inositol-1,4,5-trisphosphate receptor.

BACKGROUND ART

D-Myo-inositol-1,4,5-trisphosphate (herein occasionally abbreviated as "IP$_3$") is a second messenger that binds to the IP$_3$ receptor to cause release of Ca$^{2+}$ from the Ca$^{2+}$ storage sites in cells, and it controls kinetics of intracellular Ca$^{2+}$ concentration in variety of cells. IP$_3$ plays an important role for control of various cellular functions such as secretion, insemination, muscular contraction, nervous signal transmission and cellular growth (Berridge, M. J., Nature, 361, 315, 1993; Clapham, D. E., Cell, 80, 259, 1995).

In order to study the signal transmission induced by IP$_3$, a lot of IP$_3$ analogues have been synthesized (Li, W., et al., Nature, 392, 936, 1998; McCarren, M. et al., J. Neuron, 3, 461, 1989), and the structures of the IP$_3$ receptors and other IP$_3$ binding proteins have been examined (Mourey, R. J. et al., Biochemistry, 32, 1719, 1993). It has been reported that, even though the phosphate in the 1-position of IP$_3$ is modified, its binding affinity to the IP$_3$ receptor is not substantially affected (Schafer, R., et al., Biochem. J., 272, 817, 1990; Prestwich, G. D. et al., J. Am. Chem. Soc., 113, 1822, 1991). It is known that adenophostins, metabolites isolated from a culture of *Penicillium brevicompactum*, are most potent agonists to the IP$_3$ receptors (Takahashi, M., et al., J. Biol. Chem., 269, 369, 1994).

DISCLOSURE OF THE INVENTION

The inventors of the present invention conducted various studies to provide a novel IP$_3$ receptor ligand. As a result, they unexpectedly found that compounds having extremely high affinity to the IP$_3$ receptor can be provided by modifying the phosphate in the 1-position of IP$_3$ with a dye derivative or a fluorescent dye derivative such as malachite green and fluorescein. The present invention was achieved on the basis of the above findings.

The present invention thus provides compounds represented by the following general formula (I) or salts thereof:

(I)

wherein R represents a group represented by the following formula (A), (B) or (C):

(A)

(B)

(C)

wherein R$^1$ and R$^2$ independently represent a C$_{1-6}$ alkyl group; R$^3$ represents an amino group, a mono(C$_{1-6}$ alkyl)amino group, a di(C$_{1-6}$ alkyl)amino group, or a C$_{1-6}$ alkoxy group; and X- represents an anion, and n represents an integer of 2 to 5.

According to preferred embodiments of the present invention, provided are the aforementioned compounds or salts thereof, wherein the compounds represented by the general formula (I) are those represented by the following formula (I-1):

(I-1)

wherein R has the same meaning as that defined above; the aforementioned compounds or salts thereof, wherein R is a group represented by the formula (A) wherein R$^1$ and R$^2$ represent a methyl group, R$^3$ represents a dimethylamino group, and X- represents a chlorine ion, and n is 3; and the aforementioned compounds or salts thereof, wherein R is a group represented by the formula (A) wherein $R^1$ and $R^2$ represent a methyl group, $R^3$ represents a dimethylamino group and X- represents a chlorine ion, and n is 3.

From another aspect of the present invention, there are provided $IP_3$ receptor ligands which comprises a compound represented by the aforementioned general formula (I) or a salt thereof. $IP_3$ receptor can be denatured by binding the aforementioned $IP_3$ receptor ligand and then irradiating with light. Therefore, the $IP_3$ receptor ligands comprising the compound represented by the aforementioned general formula (I) or a salt thereof are useful as regents for denaturing the $IP_3$ receptor. The present invention also provides medicaments comprising the compound represented by the aforementioned general formula (I) or a salt thereof. These medicaments are useful as agents for prophylactic and/or therapeutic treatment of diseases resulting from supernumerary $IP_3$ or hyper-expression of the $IP_3$ receptor.

From still further aspect of the present invention, there are provided methods for denaturing the $IP_3$ receptor, which comprise the steps of binding the compound represented by the aforementioned general formula (I) or a salt thereof to the $IP_3$ receptor and then irradiating the result with light. The present invention also provides cells or cell extracts, of which $IP_3$ receptor is denatured, preferably by the aforementioned methods.

BRIEF DESCRIPTION OF THE DRAWINGS

FIG. 1A depicts the results of the surface plasmon resonance induced by IBD and BSA. FIG. 1B depicts the results of competitive assay of $IP_3$, Compound 1, Compound 2a and Compound 2b, which indicates that binding of IBD to a Compound 1-immobilized tip was inhibited by these compounds. FIG. 1C depicts the results of competitive assay of Compound 2b and carboxymalachite green (CMG) at a low concentration of IBD. The IBD concentration was 52.8 nM (B) or 1.76 nM (C).

FIG. 2A depicts the results that $Ca^{2+}$ releasing activity induced by $IP_3$ was suppressed after laser irradiation; FIG. 2B depicts the results that when laser irradiation time was changed, the $Ca^{2+}$ releasing activity was suppressed in an irradiation time-dependent manner; FIG. 2C depicts that the $Ca^{2+}$ releasing activity was not reduced only by the laser irradiation or only by the addition of Compound 2b as compared with the releasing activity in the absence of the addition of Compound 2b and the laser radiation, whereas the $Ca^{2+}$ releasing activity was remarkably reduced when both of the addition of Compound 2b and the laser radiation were applied.

BEST MODE FOR CARRYING OUT THE INVENTION

The $C_{1-6}$ alkyl group represented by $R^1$ and $R^2$ may be linear, branched cyclic, or a combination thereof. For example, methyl group, ethyl group, n-propyl group, isopropyl group, cyclopropyl group, n-butyl group, sec-butyl group, isobutyl group, cyclobutyl group, cyclopropylmethyl group, n-pentyl group, n-hexyl group, cyclohexyl group and the like may be used. It is preferred that $R^1$ and $R^2$ are methyl groups. As an alkyl group in the mono($C_{1-6}$ alkylamino) group or di($C_{1-6}$ alkyl)amino group represented by $R^3$ or an alkyl moiety in the $C_{1-6}$ alkoxy group, the $C_{1-6}$ alkyl groups explained above can be used. As $R^3$, dimethylamino group is preferred. X-represents an anion, and its type is not particularly limited. For example, a halogen ion such as a chlorine ion is preferred. Symbol n represents an integer of 2 to 5, and is preferably 3. R is preferably a group represented by the aforementioned formula (A), i.e., a residue of malachite green.

The compounds of the present invention represented by the aforementioned formula (I) can be prepared according to the following scheme.

(In the scheme, the preparation of the compound wherein n is 3 is shown.)

1D-1-O-(3-Aaminopropyl-1-(phospho)-myo-inositol-4,5-bisphosphate (Compound 1: Strupish, J., et al., Biochem. J., 253, 901, 1988) can be prepared through 14 steps from D-myo-inositol (Prestwich, G. D., et al., J. Am. Chem. Soc., 113, 1822, 1991; Ozaki, S., et al., J. Chem. Soc. Perkin Trans. I, 1992, 729; Gigg, J., et al., J. Chem. Soc. Perkin Trans. I, 423, 1987; Bannwarth, W., et al., Helv. Chim. Acta, 70, 175, 1987). The compounds of the present invention can be prepared by reacting Compound 1 to with an ester of N-hydroxysuccinimide and a fluorescein derivative or malachite green derivative or the like. For example, Compound 1 dissolved in 0.1 M $NaHCO_3$ buffer (pH 8.3) may be added with the aforementioned N-hydroxysuccinimide ester in the presence of a solvent such as dimethylformamide, and then the mixture is reacted at room temperature for 2 to 3 hours under light shielding.

The 4-(carboxymalachite green)-N-hydroxysuccinimide ester (CMG-SE), a product of esterification of N-hydroxysuccinimide, can be obtained by, for example, acylating N-hydroxysuccinimide (NHS) with an acid condensate of 4-carboxybenzaldehyde (one equivalence) and dimethylaniline (two equivalences) in the presence of N-ethyl-N'-(3-dimethylaminopropyl)carbodiimide (EDC)

hydrochloride and then oxidizing the product with 2,3-dichloro-5,6-dicyano-1,4-benzoquinone (DDQ). 5-Carboxyfluorescein-N-hydroxysuccinimide ester (CF-SE) can be obtained as a commercially available product (for example, available from Research Organics, Inc.).

The compounds of the present invention represented by the formula (I) may form salts, and any of such salts fall within the scope of the present invention. Further, the compounds may form an intramolecular ion pair (zwitterion). The compounds of the present invention may have one or more asymmetric carbons depending on the type of a substituent, and any of stereoisomers such as optically active isomers and diastereoisomers, any mixtures of stereoisomers, racemates and the like forth fall within the scope of the present invention. As for the group represented by R, tautomers may occasionally exist, and any of such tautomers fall within the scope of the present invention. Furthermore, the compounds of the present invention in free forms or salts thereof may exist as hydrates or solvates, and such substances also fall within the scope of the present invention.

The compounds represented by the aforementioned general formula (I) have high affinity to the $IP_3$ receptor, and are useful as $IP_3$ receptor ligands. Since the compounds of the present invention have a chromophore or a fluorophore, they can be used as, for example, fluorescent regents for measuring affinity of a test substance to the $IP_3$ receptor. Specific examples of such methods will be described in detail in the examples of the specification. Further, by binding the compound of the present invention to the $IP_3$ receptor and the carrying out irradiation with light, the $IP_3$ receptor to which the compound of the present invention binds can be denatured. For example, by irradiating cultured cells, cultured tissues, cell extracts and the like with light in the presence of the compound of the present invention, the $IP_3$ receptor can be denatured in vitro. Further, a laboratory animal in which the function of the $IP_3$ receptor is reduced or terminated can be created by administering the compound of the present invention to a mammal excluding a human, and then subjecting the mammal to light irradiation to denature $IP_3$ receptors in vivo.

Furthermore, for the treatment of a disease resulting from supernumerary $IP_3$ or hyper-expression of the $IP_3$ receptor, the compound of the present invention can be administered to a mammal including human as a medicament, and then the mammal can be subjected to light irradiation to reduce the function of the $IP_3$ receptor in vivo to treat the disease. Therefore, the present invention provides methods for denaturing the $IP_3$ receptor, which comprises the steps of binding the compound represented by the aforementioned general formula (I) or a salt thereof to the $IP_3$ receptor and then carrying out irradiation with light; cells or cell extracts in which the $IP_3$ receptor are denatured; and agents for denaturing the $IP_3$ receptor which comprises the aforementioned $IP_3$ receptor ligand. The condition of the light irradiation for denaturation of the $IP_3$ receptor can be chosen depending on the characteristics of a dye derivative or a fluorescent dye derivative of the aforementioned $IP_3$ receptor ligand. Usually, the irradiation can be carried out by using a laser light having a long. wavelength of about 620 nm or about 500 nm that does not affect the cells.

The medicament of the present invention comprises one or more substances selected from the group consisting of the compounds represented by the aforementioned formula (I) and salts thereof, and hydrates thereof and solvates thereof as an active ingredient. The aforementioned substances, per se, may be administered as the medicament of the present invention. Preferably, the substance may be administered as a pharmaceutical composition. The form of the pharmaceutical composition is not particularly limited, and a pharmaceutical composition for oral administration or parenteral administration can be produced by using one or more kinds of suitable additives for pharmaceutical preparations and then administered. Examples of the pharmaceutical composition suitable for oral administration include, for example, tablets, capsules, powders, subtilized granules, granules, solutions, syrups and the like. Examples of the pharmaceutical composition suitable for parenteral administration include, for example, injections, suppositories, inhalants, eye drops, nasal drops, ointments, creams, patches and the like.

The aforementioned pharmaceutical composition can be produced by adding pharmaceutically and pharmacologically acceptable additives. Examples of the pharmaceutically and pharmacologically acceptable additives include, for example, excipients, disintegrating agents or disintegrating aids, binders, lubricants, coating agents, dyes, diluents, bases, dissolving agents or dissolving aids, isotonic agents, pH modifiers, stabilizers, propellants, adherent and the like.

Doses of the medicament of the present invention are not particularly limited. The doses can be suitably chosen depending on the type of action and potency of the action of the medicament, and suitably increased or decreased depending on various factors to be ordinarily considered such as the body weight and age of a patient, the type and symptoms of a disease, an administration route and the like. For example, for oral administration, the medicament can be used in an amount of from 0.01 to 1,000 mg per day for an adult. After the medicament of the present invention is administered, therapeutic or prophylactic treatment of a disease resulting from supernumerary $IP_3$ or hyper-expression of the $IP_3$ receptors can be conducted by performing light irradiation at a strength sufficient for reducing the function of the $IP_3$ receptor in vivo. Strength and frequency of the light irradiation can suitably be chosen by those skilled in the art depending on a dose and an administration route of the medicament of present invention, the type of a disease, the body weight and age of a patient and the like.

EXAMPLES

The present invention will be more specifically explained with reference to the following examples. However, the scope of the present invention is not limited to the following examples.

Example 1

Preparation of Compounds 1D-1-O-(3-Aminopropyl-1-(phospho)-myo-inositol-4,5-bisphosphate (Compound 1 shown in the aforementioned scheme, Strupish J., et al., Biochem. J., 253, 901, 1988) was prepared according to a method described in the literature (Prestwich, G. D., et al., J. Am. Chem. Soc., 113, 1822, 1991; Ozaki, S., et al., J. Chem. Soc. Perkin Trans. I, 1992, 729; Gigg, J., et al., J. Chem. Soc. Perkin Trans. I, 423, 1987; Bannwarth, W., et al., Helv. Chim. Acta, 70, 175, 1987). N-Hydroxysuccinimide (NHS) was acylated in the presence of N-ethyl-N'-(3-dimethylaminopropyl)-carbodiimide (EDC) hydrochloride by using an acid condensation product of 4-carboxybenzaldehyde (one equivalence) and dimethylaniline (two equivalences) as an acylation agent. Then, the product was oxidized with 2,3-dichloro-5,6-dicyano-1,4-benzoquinone (DDQ) to obtain 4-(carboxymalachite green)-N-hydroxysuccinimide ester (CMG-SE).

Compound 1 in 0.1 M NaHCO$_3$ buffer (pH 8.3) was added with 5-carboxy-fluorescein-N-hydroxysuccinimide ester (CF-SE, Research Organics, Inc.) or CMG-SE, and then the reaction mixture was stirred at room temperature for 2 to 3 hours to obtain Compound 2a or 2b mentioned in the aforementioned scheme, respectively. CMG-SE, Compounds 2a, and 2b were purified by C$_{18}$ reverse phase HPLC. The optical purities of the aforementioned compounds were calculated from the specific rotation of 1D-4,5-di-O-allyl-3,6-di-O-benzyl-1-1-methoxyacetyl-myo-inositol (intermediate product of Compound 1, Ozaki, S., et al., J. Chem. Soc. Perkin Trans. I, 729, 1992).

Spectrum data (Radenberg, T., et al., Biochem. J., 264, 323, 1989): 1D-4,5-di-O-allyl-3,6-di-O-benzyl-1-1-methoxyacetyl-myo-inositol: $[\alpha]^{25}_D = -52.5$ (c 2.2, CHCl$_3$): 4-(Carboxymalachite green)-N-hydroxysuccinimide ester (CMG-SE): $^1$H-NMR (CDCl$_3$) δ 2.96 (s, 4H), 3.37(s, 12H), 6.96 (d, J =8.79 Hz, 4H), 7.37 (d, J=8.79 Hz,4H), 7.49(d, J=8.22 Hz, 2H), 8.29 (d, J=8.22 Hz, 2H); FABMS 470(M)+; Compound 2a: $^1$H NMR (D$_2$O) δ 1.88 (m, 2H), 3.46 (m,2H), 3.58(dd, J=2.37, 9.78 Hz, 1H), 3.77 (t, J=9.15 Hz, 1H), 3.87–4.00 (m, 4H), 4.14 (t, J=2.19 Hz, 1H), (dd, J=8.79, 9.69 Hz, 1H), 6.96 (dd, J=2.19, 9.24 Hz, 2H), 7.08(d, J=2.19 Hz, 2H), 7.29 (d, J=9.15 Hz, 2H), 7.38 (d, J=7.71 Hz, 1H), 8.07 (dd, J=1.65, 7.95 Hz, 1H), 8.50 (d, J=1.11 Hz, 1H); FABMS 836 (MH)$^+$; Compound 2b: $^1$H NMR(D$_2$O) δ 1.80 (m, 2H), 3.14 (s, 12H), 3.35 (m, 2H), 3.47 (dd, J=2.58, 9.80 Hz, 1H), 3.69 (t, J=9.54 Hz, 1H), 3.82–3.97 (m, 4H), 4.07 (t, J=2.91 Hz, 1H), 4.21 (dd, J=6.21, 9.54 Hz, 1H), 7.20 (d, J=8.25 Hz, 2H), 7.32 (d, J=8.79 Hz:, 4H), 7.46 (d, J=8.97 Hz, 4H), 7.59 (d, J=8.43 Hz, 2H); FABMS 832 (M)$^+$.

Example 2

Binding Assay (1) Expression and Purification of Human IP$_3$ Receptor Type 1

The IP$_3$ binding domain (IBD, amino acid residues 1-885, Mignery, G. A., et al., EMBO J., 9, 3893, 1990) of human IP$_3$ receptor type 1 (Yamada, N., et al., Biochem. J., 302, 781, 1994) was subcloned in pGEX2T (Amersham Pharmacia) for expression in bacteria. The N-terminus of IBD was fused to glutathione S-transferase using a linker sequence Leu-Val-Pro-Arg-Gly-Ser, whilst the C-terminus of IBD was labeled at His using a linker sequence Leu-Val-Pro-Arg-Gly-Ser. The protein was expressed in *Escherichia coli* BL-21 (DE3), and a recombinant protein was purified by using a resin on which Ni-NTA was immobilized (Amersham Pharmacia) and a HiTrap NHS-activated affinity column (Amersham Pharmacia) to which Compound 1 was bound. The purity of protein was calculated as 22% based on the result from SDS-PAGE.

(2) Measurement of Surface Plasmon Resonance

Surface plasmon resonance (SPR) was measured by using BIAcore 2000 (Amersham Pharmacia). After activation with NHS and EDC, 10 mM of Compound 1 in 100 mM borate buffer (pH 8.5) was bound to the surface of CM5 sensor tip, and inactivated with ethanolamine. In order to determine dissociation constants of IP$_3$, Compound 1, Compound 2a, and Compound 2b, IBD purified beforehand was dissolved in a mobile phase buffer (10 mM HEPES, 150 mM NaCl, 3.4 mM EDTA and 0.005% Tween20, pH 7.4) together with each of the compounds. After each sample was injected, the tip surface was regenerated with 100 mM NaOH.

Figure 1:
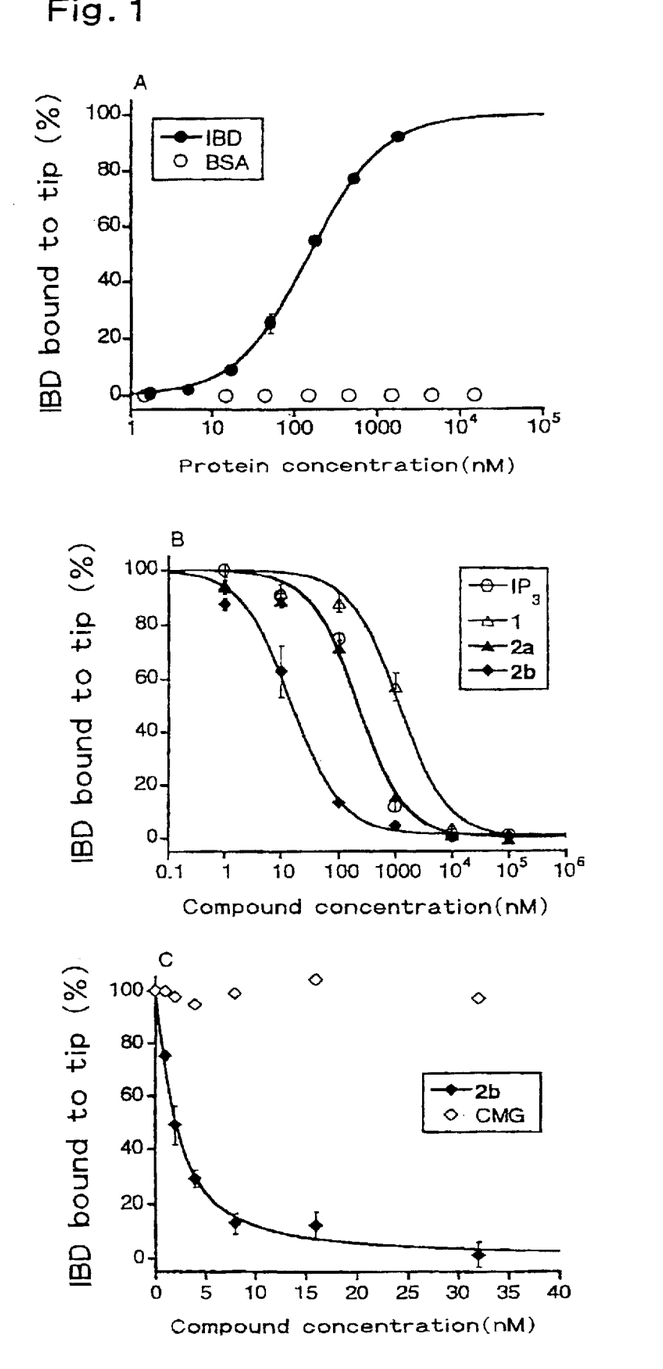
FIG. 1 shows that the compounds of the present invention act as $IP_3$ receptor ligands. In the figure.

IBD bound to the tip in a concentration-dependent manner, however, non-specific binding with BSA (or glutathione S-transferase) was not observed. From these results, obtained by injecting the IBD or bovine serum albumin (BSA) at various concentrations (FIG. 1A), it was revealed that the Compound 1-immobilized sensor tip was suitable for this assay. In order to determine affinity of IP$_3$, Compound 1, Compound 2a and Compound 2b to IBD, a competitive assay was performed as follows. IBD (52.8 nM) was mixed with each of the aforementioned compounds at various concentrations. When the mixture was introduced onto the tip, a compound that competed with Compound 1 was bound to IBD and thereby immobilized on the tip surface (FIG. 1B). SPR obtained from this assay was applied to the equation to calculate dissociation constant (Kd) of each compound.

(3) Calculation of Dissociation Constants

For calculation of K$_d$ of each compound, the resulting data plotted in FIGS. 1B and 1C were applied to the formula:
$$100[1-[X+Y+K_d-\{X^2+2X\ (K_d-Y)+(K_d+Y)^2\}^{1/2}]/2Y]$$
wherein X and Y are a concentration of each compound and IBD concentration, respectively. Since K$_d$ of Compound 2b was considerably lower than the half of the IBD concentration, the value was not calculated accurately. Therefore, the IBD concentration was lowered to 1.76 nM, and the competitive assay for Compound 2b was performed again (FIG. 1C). The binding assay was carried out under a light condition and under a dark condition to verify that the binding was not affected by light. In order to calculate non-specific binding of Compound 2b to the IP$_3$ receptor, carboxymalachite green (CMG, the hydrophobic moiety of Compound 2b) was injected during the competitive assay (FIG. 1C), and as a result, non-specific binding was not observed. Therefore, it was demonstrated that Compound 2b specifically bound to the IP$_3$ receptor.

The affinity of Compound 1 was about ⅙ of that of IP$_3$ (Prestwich, G. D., et al., J. Am. Chem. Soc., 113, 1822, 1991), whereas the affinity of Compound 2a was almost the same as that of IP$_3$, and Compound 2b had 167-fold higher affinity than IP$_3$ (Table 1).

TABLE 1

| Compound | K$_d$ [nM] |
| --- | --- |
| IP$_3$ | 195 |
| 1 | 1100 |
| 2a | 188 |
| 2b | 1.17 |

Example 3

Denaturation of the IP$_3$ Receptor by Light Irradiation by Using the Compound of the Present Invention (1) Preparation of a Tissue Specimen A strip of smooth muscle tissue prepared from a portal vein of male guinea pigs (weight 200–300 g) was fixed on a stainless steel wire to prepare a tissue specimen.

(2) Measurement of Ca$^{2+}$ Releasing Activity

The above specimen was incubated at 35° C. for 3.5 hours in a 40 μM solution of mag-fura-2 AM (Molecular Probes) as a Ca$^{2+}$ fluorescent indicator to have the mag-fura-2 AM taken up by the specimen. Subsequently, the specimen was incubated at 35° C. for 1.5 to 2 hours in a 40–60 μM solution of β-escin as a surfactant to remove the mag-fura-2 AM present other than in intracellular organelles.

The specimen was inserted into a glass capillary, and then initial change of fluorescence intensity ratio (fluorescence intensity at Ex. 340 nm, Em.480 nm/fluorescence intensity at Ex. 375 nm, Em. 480 nm, i.e., releasing rate), at addition of various solutions to the specimen, was fitted to an exponential curve to obtain a value as Ca²⁺ releasing activity. As the fluorescence photometer, CAF-110 (JASCO) was used.

(3) Method for Denaturing the IP₃ Receptor by Light Irradiation Using the Compound of the Present Invention The tissue specimen prepared in the above (1) was added with 1 μM IP₃, and its Ca²⁺ releasing activity was measured (before irradiation). This specimen was removed from a fluorescence photometer after the measurement, and the inside of a capillary was filled with 1 μM solution of Compound 2b. The specimen was then irradiated with laser for 3 minutes, while prevented from drying by pipetting operation.

After the laser irradiation, the specimen was again placed on the fluorescence photometer, and then added with 1 μM IP₃ to determine the Ca²⁺ releasing activity. The results (after the irradiation) were compared with the values obtained before the irradiation. It took allover 2.5 minutes to take out the specimen from the fluorescence photometer, add Compound 2b, and then start the irradiation, and it also took 1.5 minutes to return the specimen to the fluorescence photometer after the completion of the laser irradiation (i.e., the operation time was irradiation time+4 minutes). For a control experiment in which laser irradiation was not applied, the specimen was added with Compound 2b, and after 2.5 minutes, the specimen was subjected only to pipetting operation for 3 minutes and left for 1.5 minutes, and then the measurement was continued. The result of "0 minute" of the irradiation time in the experiment where irradiation time was varied, the specimen was filled with a solution of Compound 2b and left for 4 minutes, and then the measurement was started. As the laser, YAG: Nd-pumped day laser (wavelength 635 nm, pulsed 2–4 ns, 15 mJ per pulse at 10 Hz, 3 mm diameter laser spot, Continuum) was used.

Figure 2:
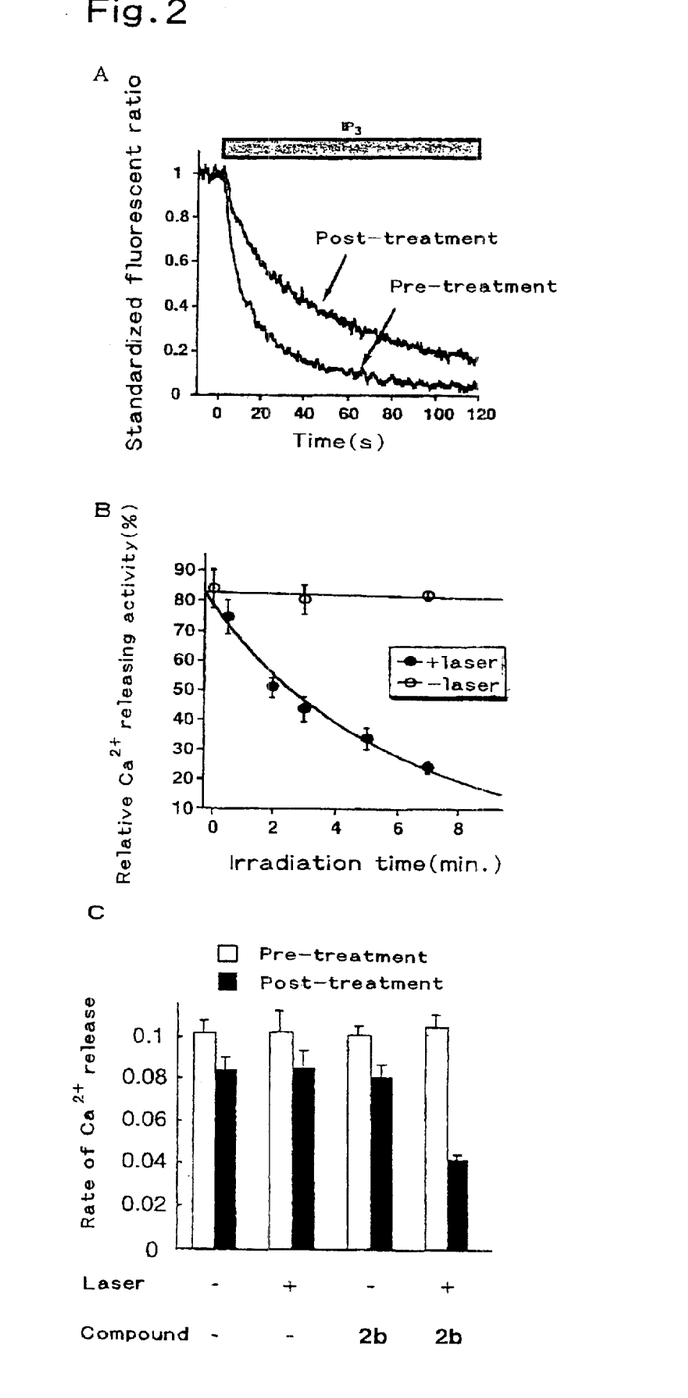
FIG. 2 shows that the $IP_3$ receptor was successfully denatured by binding a compound of the present invention with the $IP_3$ receptor and then carrying out irradiation with light.

Suppression of the Ca²⁺ releasing activity induced by IP₃ was observed after the laser irradiation (FIG. 2A). When the laser irradiation time was varied, the Ca²⁺ releasing activity was suppressed in an irradiation time-dependent manner (FIG. 2B). The Ca²⁺ releasing activity was not reduced under a condition of laser irradiation alone or mere addition of Compound 2a compared with the releasing activity obtained under a condition without the addition of Compound 2a and laser irradiation. Whilst marked reduction of the Ca²⁺ releasing activity was observed when both of laser irradiation and addition of Compound 2a were applied (FIG. 2C).

From the above results, it was verified that the IP₃ receptor bound with the compound of the present invention can be denatured by binding a compound of the present invention to the IP₃ receptor and applying light irradiation.

Industrial Applicability

The compounds represented by the aforementioned general formula (I) and salts thereof have a property of binding to the IP₃ receptor as a ligand. For example, the IP₃ receptor can be denatured by binding the IP₃ receptor ligand to the IP₃ receptor, and then applying light irradiation. Therefore, they are useful as an active ingredient of medicaments.

What is claimed is:

1. A compound represented by the following general formula (I) or a salt thereof:

wherein R represents a group represented by the following formula (A), (B) or (C):

wherein $R^1$ and $R^2$ independently represent a $C_{1-6}$ alkyl group, $R^3$ represents an amino group, a mono($C_{1-6}$ alkyl) amino group, a di($C_{1-6}$ alkyl)amino group, or a $C_{1-6}$ alkoxy group, and X-represents an anion, and n represents an integer of 2 to 5.

2. The compound or a salt thereof according to claim 1, wherein the compound represented by the general formula (I) is a compound represented by the following formula (I-1):

(I-1)

wherein R has the same meaning as that defined above.

3. The compound or a salt thereof according to claim 1, wherein R is a group represented by the formula (A) wherein $R^1$ and $R^2$ represent a methyl group, $R^3$ represents a dimethylamino group, and X-represents a chlorine ion, and n is 3.

4. An $IP_3$ receptor ligand, which comprises a compound or a salt thereof according to claim 1.

5. A method for denaturing an $IP_3$ receptor, which comprises the steps of binding a compound or a salt thereof according to claim 1 to the $IP_3$ receptor and applying irradiation with light.

6. A cell or a cell extract in which an $IP_3$ receptor is denatured by the method according to claim 5.

7. A regent for denaturation of an $IP_3$ receptor, which comprises a compound or a salt thereof according to claim 1.

8. A medicament comprising a compound or a physiologically acceptable salt thereof according to claim 1.

9. The compound or a salt thereof according to claim 2, wherein R is a group represented by the formula (A) wherein $R^1$ and $R^2$ represent a methyl group, $R^3$ represents a dimethylamino group, and X-represents a chlorine ion, and n is 3.

10. An $IP_3$ receptor ligand, which comprises a compound or a salt thereof according to claim 2.

11. An $IP_3$ receptor ligand, which comprises a compound or a salt thereof according to claim 3.

12. An $IP_3$ receptor ligand, which comprises a compound or a salt thereof according to claim 9.

13. A method for denaturing an $IP_3$ receptor, which comprises the steps of binding a compound or a salt thereof according to claim 2 to the $IP_3$ receptor and applying irradiation with light.

14. A method for denaturing an $IP_3$ receptor, which comprises the steps of binding a compound or a salt thereof according to claim 3 to the $IP_3$ receptor and applying irradiation with light.

15. A method for denaturing an $IP_3$ receptor, which comprises the steps of binding a compound or a salt thereof according to claim 9 to the $IP_3$ receptor and applying irradiation with light.

16. A cell or a cell extract in which an $IP_3$ receptor is denatured by the method according to claim 13.

17. A cell or a cell extract in which an $IP_3$ receptor is denatured by the method according to claim 14.

18. A cell or a cell extract in which an $IP_3$ receptor is denatured by the method according to claim 15.

19. A regent for denaturation of an $IP_3$ receptor, which comprises a compound or a salt thereof according to claim 2.

20. A regent for denaturation of an $IP_3$ receptor, which comprises a compound or a salt thereof according to claim 3.

21. A regent for denaturation of an $IP_3$ receptor, which comprises a compound or a salt thereof according to claim 9.

22. A medicament comprising a compound or a physiologically acceptable salt thereof according to claim 2.

23. A medicament comprising a compound or a physiologically acceptable salt thereof according to claim 3.

24. A medicament comprising a compound or a physiologically acceptable salt thereof according to claim 9.

* * * * *

UNITED STATES PATENT AND TRADEMARK OFFICE
CERTIFICATE OF CORRECTION

PATENT NO.    : 6,656,927 B1
DATED         : December 2, 2003
INVENTOR(S)   : T. Nagano et al.

It is certified that error appears in the above-identified patent and that said Letters Patent is hereby corrected as shown below:

Title page,
Item [54], Title, "LIGANDS" should be -- LIGAND --
Item [73], Assignees, "Daiichi Pharmaceutical., Ltd." should be -- Daiichi Pharmaceutical Co., Ltd. --.

Signed and Sealed this

Fourteenth Day of September, 2004

JON W. DUDAS
*Director of the United States Patent and Trademark Office*